US010551350B2

(12) United States Patent
Cheng et al.

(10) Patent No.: US 10,551,350 B2
(45) Date of Patent: Feb. 4, 2020

(54) METHOD FOR SIMULATING MAGNETIC FLUX LEAKAGE BASED ON LOOP CURRENT

(71) Applicant: UNIVERSITY OF ELECTRONIC SCIENCE AND TECHNOLOGY OF CHINA, Chengdu, Sichuan (CN)

(72) Inventors: Yuhua Cheng, Chengdu (CN); Libing Bai, Chengdu (CN); Yonggang Wang, Chengdu (CN); Jie Zhang, Chengdu (CN); Chun Yin, Chengdu (CN); Shuai Shi, Chengdu (CN); Xue Chen, Chengdu (CN)

(73) Assignee: UNIVERSITY OF ELECTRONIC SCIENCE AND TECHNOLOGY OF CHINA, Chengdu (CN)

( * ) Notice: Subject to any disclaimer, the term of this patent is extended or adjusted under 35 U.S.C. 154(b) by 294 days.

(21) Appl. No.: 15/681,186

(22) Filed: Aug. 18, 2017

(65) Prior Publication Data
US 2018/0335403 A1 Nov. 22, 2018

(30) Foreign Application Priority Data
May 16, 2017 (CN) .......................... 2017 1 0344531

(51) Int. Cl.
*G01N 27/82* (2006.01)
*G06F 17/50* (2006.01)
*G01N 27/83* (2006.01)
(52) U.S. Cl.
CPC ............. *G01N 27/82* (2013.01); *G01N 27/83* (2013.01); *G06F 17/5009* (2013.01)

(58) Field of Classification Search
CPC ..... G01N 27/82; G01N 27/83; G06F 17/5009
USPC .......................................................... 702/58
See application file for complete search history.

(56) References Cited

U.S. PATENT DOCUMENTS

| 2015/0316508 | A1* | 11/2015 | Lee ........................ G01N 27/83 324/229 |
| 2018/0038833 | A1* | 2/2018 | Iannucci ................ G01N 27/82 |

OTHER PUBLICATIONS

Dutta et al., "Dipole Modeling of Magnetic Flux Leakage," IEEE Transactions on Magnetics, Apr. 2009, vol. 45, No. 4, pp. 1959-1965.

(Continued)

*Primary Examiner* — Michael P Nghiem
*Assistant Examiner* — Dacthang P Ngo
(74) *Attorney, Agent, or Firm* — Oliff PLC (57) ABSTRACT

The present invention provides a method for simulating magnetic flux leakage based on loop current, the magnetic distribution of a single loop current is obtained by solid angle, then the magnetic field distribution of a semi-infinite solenoid is obtained based on the assumption of arrangement of loop currents in the magnetized specimen, and its equation is given; and the JA hysteresis model is introduced to obtain the distribution of quasi-static magnetic flux leakage field, on the basis of analyzing the relation between the distribution of a loop current on the surface of the defect and the excitation magnetic field, the distribution of quasi-static magnetic flux leakage field is obtained based on the semi-infinite solenoid.

2 Claims, 4 Drawing Sheets

(56) References Cited

OTHER PUBLICATIONS

Edwards et al., "The magnetic leakage field of surface-breaking cracks," J. Phys. D: Appl. Phys., 1986, vol. 19, pp. 657-673.
Wang et al., "Velocity effect analysis of dynamic magnetization in high speed magnetic flux leakage inspection," NDT&E International, 2014, vol. 64, pp. 7-12.

\* cited by examiner

METHOD FOR SIMULATING MAGNETIC FLUX LEAKAGE BASED ON LOOP CURRENT

CROSS-REFERENCE TO RELATED APPLICATIONS

This application claims priority under the Paris Convention to Chinese Patent Application No. 201710344531.6, filed May 16, 2017, the entirety of which is hereby incorporated by reference for all purposes as if fully set forth herein.

FIELD OF THE INVENTION

The present invention relates to the field of simulating magnetic flux leakage in defect detection, more particularly to a method for simulating magnetic flux leakage based on loop current.

BACKGROUND OF THE INVENTION

The methods for simulating magnetic flux leakage in defect detection can be categorized into analytical method based on magnetic dipole model and finite element method (FEM) based on Maxwell's equations. However, both methods have certain limitations. For instance, the analytical method based on magnetic dipole model omits the nonlinear magnetization of ferromagnetic material and the geometric parameters of defect, and the results of magnetic dipole model are highly dependent on the setting of magnetic dipole distribution, which leads to unsuitability for complex defect. As for the FEM, it can't get the functional relationship between the magnetic flux leakage signal and the shape of defect, and the calculation process of FEM is highly dependent on meshing, thus high-precision calculation will consume considerable computing resources and time.

SUMMARY OF THE INVENTION

The present invention aims to overcome the deficiencies of prior art and provides a method for simulating magnetic flux leakage based on loop current, which can be applied to complex defect and obtain the functional relationship between the magnetic flux leakage signal and the shape of defect.

To achieve these objectives, in accordance with the present invention, a method for simulating magnetic flux leakage based on loop current is provided, comprising the following steps:

(1) Establishment of homogeneous magnetization of a flat ferromagnetic specimen (hereinafter referred to as "Specimen")

placing a specimen in an excitation magnetic field, where the excitation magnetic field is uniform, the direction of the excitation magnetic field is the positive direction of an x-axis, the intensity value of the excitation magnetic field is $H_{ex}$, and when the magnetization value of saturation area of the specimen is $M_{s\_sp}$ and the proportion of saturation area of the specimen is $k_s$, the specimen is regarded as a homogeneous magnetized body;

applying a solenoid model to the end faces of the specimen, and under the interaction between the excitation magnetic field and the end faces of the specimen, the magnetic field intensity $\vec{H}_{air}$ at the borderline between saturation area and insaturation area of the specimen in the air is:

$$\vec{H}_{air} = \vec{H}_{ex} + (M_{s\_sp} \vec{r}_{air} ds)/(4\pi r_{air}^3) \quad (1)$$

where $\vec{H}_{ex}$ is the intensity of the excitation magnetic field, $\vec{r}_{air}$ is a vector from an end face element ds to a point in air domain;

substituting the x-axis component $\vec{H}_{x\_sp}$ of the magnetic field intensity in the specimen into a Jiles Atherton (JA) hysteresis model, and obtaining the magnetization $\vec{M}_{x\_sp}$ in the specimen, where the x-axis component $\vec{H}_{z\_sp}$ is equal to the x-axis component $\vec{H}_{x\_air}$ of magnetic field intensity $\vec{H}_{air}$; taking the specimen as a homogeneous magnetized body which is already saturated, when $M_{x\_sp} > k_M * M_{s\_sp}$, where $k_M$ is a proportionality constant which is smaller than 1, and the proportionality constant $k_s$ and $k_M$ are determined by the precision of magnetic flux leakage simulation, and the larger they are, the more precise the simulation is;

(2) Simulation of magnetic flux leakage based on loop current on the condition of omitting the interacting forces between solenoids according to the theory of molecular current, assuming that the loop currents in the specimen are homogeneous, when the specimen is placed in the excitation magnetic field which is uniform and has a same direction with the positive direction of the x-axis;

2.1) Calculation of the magnetic field distribution of a semi-infinite solenoid obtaining a magnetic flux density $\vec{B}_{cp}$ generated by a loop current at a point P, where the point P is in the half-space that the magnetic moment of the loop current points to, and the magnetic flux density $\vec{B}_{cp}$ is:

$$\vec{B}_{cp} = -\frac{\mu_0 I}{4\pi} \nabla \Omega \quad (2)$$

where $\Omega = (S \cos \gamma)/r_c^2$ is the solid angle from the point P to the loop current, S is the area encircled by the loop current, $r_c$ is the distance from the center of the loop current to the point P, $\gamma$ is the angle between the axis of the loop current and the line connecting the point P and the center of the loop current, and I is the value of the loop current, $\mu_0$ is the permeability of vacuum, $\pi$ is Pi;

assuming that a series of the loop currents are densely arranged along the direction of magnetization in the specimen forming a solenoid, thus a series of the solenoids are densely arranged in the specimen, and when no defect exists on the specimen, there is no magnetic flux leakage, when there is a defect on the specimen, the value of the loop current at the surface of the defect equals to the value of the corresponding solenoid which the loop current belongs to, and the length of the corresponding solenoid is semi-infinite;

integrating the equation (2), and obtaining a magnetic flux density $\vec{B}_{sp}$ generated by a semi-infinite solenoid in the air domain:

$$\vec{B}_{sp} = \frac{\mu_0 n P_m}{4\pi} \frac{\vec{r}_s}{r_s^3} \quad (3)$$

where n is the linear density of the loop currents arranged in the semi-infinite solenoid, $\vec{P}_m$ is the magnetic moment of the loop currents arranged in the semi-infinite solenoid, the modulus of magnetic moment $\vec{P}_m$ is $P_m$, $P_m = SI$, and the relation between the direction of the magnetic moment $\vec{P}_m$ and the screw direction of the loop currents comply with the right hand screw rule, $\vec{r}_s$ is a vector from the end point of the semi-infinite solenoid to field point, and $r_s$ is the modulus of $\vec{r}_s$;

where if the axial direction of the semi-infinite solenoid is perpendicular to the surface of the defect, the magnetic flux completely leaks, and if the axial direction of the semi-infinite solenoid and the surface of the defect are parallel to each other, the magnetic flux completely does not leak;

taking the component of the magnetic moment $\vec{P}_m$ in the direction of the normal vector $\vec{m}$ of the surface of the defect as an effective component $\vec{P}_{me}$, i.e. $P_{me} = \vec{P}_m \cdot \vec{m}$, where $\vec{m}$ points to air domain, thus, obtaining a magnetic flux density $\vec{B}_{ls}$ generated by an area on the surface of the defect where a loop current is located:

$$\vec{B}_{ls} = \frac{\mu_0 n P_{me}}{4\pi} \frac{\vec{r}_s}{r_s^3} \quad (4)$$

according to the relation of magnetic flux density and magnetic field intensity in vacuum, i.e. $\vec{B}_{ls} = \mu_0 \vec{H}_{ls}$, obtaining a magnetic field intensity $\vec{H}_{ls}$ generated by an area on the surface of the defect where a loop current is located:

$$\vec{H}_{ls} = \frac{n P_{me}}{4\pi} \frac{\vec{r}_s}{r_s^3} \quad (5)$$

applying the calculation of equation (5) to other surfaces of the specimen, thus, obtaining the magnetic field distribution of semi-infinite solenoids.

2.2) Simulation of magnetic flux leakage on the condition of introducing JA hysteresis model and omitting the interacting forces between solenoids;

substituting the intensity value $H_{ex}$ of the excitation magnetic field into a JA hysteresis model, and calculating the magnetization value $M_d$ at the surface of the defect, thus obtaining the magnetization $\vec{M}_d$ at the surface of the defect, for the direction of the intensity $\vec{H}_{ex}$ of the excitation magnetic field is the same as that of the magnetization $\vec{M}_d$, then obtaining the effective component $M_{de}$ of magnetization $\vec{M}_d$, i.e. $M_{de} = \vec{M}_d \cdot \vec{m}$, where $\vec{m}$ is the normal vector $\vec{m}$ of the surface of the defect;

obtaining the magnetic field density $\vec{H}_{ld}$ at point A in the magnetic flux leakage field generated by a element ds at the surface of the defect according to equation (5):

$$\vec{H}_{ld} = \frac{M_{de}}{4\pi} \frac{\vec{r}_l}{r_l^3} ds \quad (6)$$

where $\vec{r}_l$ is the vector from ds to point A, and $r_l$ is the modulus of $\vec{r}_l$;

thus obtaining a contribution of a element on the surface of a defect to magnetic flux leakage, meanwhile, taking the end surface of the specimen as a surface of a defect and applying the equation (6) to the end surface of the specimen, obtaining the a contribution of a element on the end surface of the specimen to magnetic flux leakage, then integrating along the surface of the defect and the end surface of the specimen, and obtaining the distribution of quasi-static magnetic flux leakage field on the condition of omitting the interacting forces between solenoids, i.e. simulation of magnetic flux leakage;

(3) Simulation of magnetic flux leakage on the condition of introducing interacting forces between solenoids at the surface of the specimen separating the surface of the defect into two parts based on positive and negative effective component of the magnetization, and equally arranging 3×3 solenoids at the two parts to simulating the sources of interacting forces, where the value of the effective component of the magnetization is the magnetization value $M_{s\_sp}$ of the saturation area of the specimen;

calculating the effective component of the magnetization of each solenoid at the surface of the defect under the action of the excitation magnetic field based on JA hysteresis model, taking the sign of the effective component of the magnetization of each solenoid, and obtaining a new effective magnetization of each solenoid by combing the sign with the magnetization value $M_{s\_sp}$ then calculating the magnetic field density $\vec{H}_{ld}$ under the action of the excitation magnetic field and the 3×3 sources of interacting forces according to equation (6), taking the direction of the magnetic field density $\vec{H}_{ld}$ as the direction of magnetization $\vec{M}_d$ and obtaining a corrected effective component $M_{de}$ of magnetization $\vec{M}_d$, i.e. $M_{de} = \vec{M}_d \cdot \vec{m}$, where $\vec{m}$ is the normal vector $\vec{m}$ of the surface of the defect;

creating a rectangle for each source, where the rectangle is adjacent to the outline of source, setting the corrected effective component of magnetization in a rectangle to the mean value of those of its four sides, thus, obtaining a final corrected effective component $M_{de}$ of magnetization;

applying equation (6) to the surface of the defect and the end surface of the specimen with the final corrected effective component $M_{de}$ of magnetization, and integrating along the surface of the defect and the end surface of the specimen, thus obtaining the distribution of quasi-static magnetic flux leakage field on the condition of introducing the interacting forces between solenoids, i.e. simulation of magnetic flux leakage.

The objectives of the present invention are realized as follows:

In the present invention, i.e. a method for simulating magnetic flux leakage based on loop current, the magnetic distribution of a single loop current is obtained by solid angle, then the magnetic field distribution of a semi-infinite solenoid is obtained based on the assumption of arrangement of loop currents in the magnetized specimen, and its equation is given; and the JA hysteresis model is introduced to obtain the distribution of quasi-static magnetic flux leakage field, on the basis of analyzing the relation between the distribution of a loop current on the surface of the defect and the excitation magnetic field, the distribution of quasi-static magnetic flux leakage field is obtained based on the semi-infinite solenoid.

Meanwhile, the present invention, i.e. a method for simulating magnetic flux leakage based on loop current has the advantageous effects as follows:

(1) If the size of a specimen is known, for a given solving error of magnetization at the surface of the defect, the proportion of saturation area of the specimen and the intensity value of the excitation magnetic field can be obtained by experiment;

(2) If an analysis formula of the surface of the defect is given, according to the setup of experiment, which includes the intensity of the excitation magnetic field and the property of the specimen, the quasi-static distribution of magnetic flux leakage field can be obtained;

(3) Under static excitation, when the size of defect is small enough to ignore the inhomogeneous distribution of effective component of magnetization, or just ignoring it, the present invention can be converted to traditional magnetic dipole model.

The present invention overcomes the deficiencies of magnetic dipole model by introducing JA hysteresis model and normal vector of the surface of the defect, and the model formula of the present invention is also simple and effective. In contrast to finite element method, the present invention is more efficient, and the functional relationship between the magnetic flux leakage signal and the shape of defect can be derived from the model formula.

BRIEF DESCRIPTION OF THE DRAWING

The above and other objectives, features and advantages of the present invention will be more apparent from the following detailed description taken in conjunction with the accompanying drawings, in which.

DETAILED DESCRIPTION OF THE PREFERRED EMBODIMENT

Hereinafter, preferred embodiments of the present invention will be described with reference to the accompanying drawings. It should be noted that the similar modules are designated by similar reference numerals although they are illustrated in different drawings. Also, in the following description, a detailed description of known functions and configurations incorporated herein will be omitted when it may obscure the subject matter of the present invention.

Figure 1:
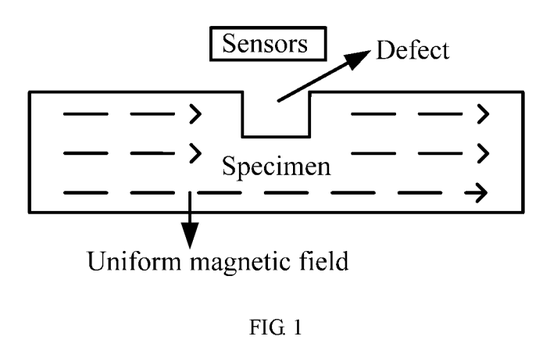
FIG. 1 is a diagram of simulating magnetic flux leakage based on loop current.

FIG. 1 is a diagram of simulating magnetic flux leakage based on loop current In one embodiment, as shown in FIG. 1, if there is a defect in a flat ferromagnetic specimen (hereinafter referred to as "Specimen"), and when the specimen is magnetized under uniform excitation magnetic field, a magnetic flux leakage field above the defect will be generated. Using sensors to measure the magnetic flux leakage field, we know if there exists a defect. But to quantify the size of the defect, we need to establish the functional relationship of the parameters in the conversion from the excitation magnetic field to magnetic flux leakage field, i.e. obtain the distribution of magnetic flux leakage field based on the excitation magnetic field and the parameters of the defect, thus a simulation of magnetic flux leakage is finished.

In simulation of magnetic flux leakage, the specimen should be in homogeneous magnetization. Therefore, in steps of the present invention, the first step is establishing the specimen as homogeneous magnetization, then theoretically analyzing the magnetic flux leakage field, and deriving the model of the distribution of magnetic flux leakage field, after that, creating a model of quasi-static magnetic flux leakage field with magnetization of the specimen by introducing the interacting forces of the sources of magnetic flux leakage field.

The details of the present invention is described hereinafter, and the method for simulating magnetic flux leakage based on loop current comprises the following steps:

Step S1: Establishment of homogeneous magnetization of a flat ferromagnetic specimen (hereinafter referred to as "Specimen")

Placing a specimen in an excitation magnetic field, where the excitation magnetic field is uniform, the direction of the excitation magnetic field is the positive direction of an x-axis, the intensity value of the excitation magnetic field is $H_{ex}$.

To create a simple but effective model, the specimen is regarded as a homogeneous magnetized body in the present invention. For the process of the magnetization of ferromagnetic materials is nonlinear, in a state of homogeneous magnetized body, the specimen must be in saturation in a state. when the magnetization value of saturation area of the specimen is $M_{s\_sp}$ and the proportion of saturation area of the specimen is $k_s$, the specimen is regarded as a homogeneous magnetized body. In one embodiment, the proportion of saturation area of the specimen is ¾, i.e. $k_s=¾$.

Applying a solenoid model to the end faces of the specimen, and under the interaction between the excitation magnetic field and the end faces of the specimen, the magnetic field intensity $\vec{H}_{air}$ at the borderline between saturation area and insaturation area of the specimen in the air is:

$$\vec{H}_{air}=\vec{H}_{ex}+(M_{s\_sp}\vec{r}_{air}ds)/(4\pi r_{air}^3) \quad (1)$$

where $\vec{H}_{ex}$ is the intensity of the excitation magnetic field, $\vec{r}_{air}$ is a vector from an end face element ds to a point in air domain.

Substituting the x-axis component $\vec{H}_{s\_sp}$ of the magnetic field intensity in the specimen into a JA hysteresis model, and obtaining the magnetization $\vec{M}_{s\_sp}$ in the specimen, where the x-axis component $\vec{H}_{x\_sp}$ is equal to the x-axis component $\vec{H}_{x\_air}$ of magnetic field intensity $\vec{H}_{air}$; taking the specimen as a homogeneous magnetized body which is already saturated, when $M_{x\_sp}>k_M*M_{s\_sp}$. In one embodiment, the proportionality constant is 0.95, i.e. $k_M=0.95$.

In one embodiment, when $k_M=0.95$ and $k_s=¾$, the relative error of the magnetic field intensity at the surface of a defect is about 10% in comparison with the magnetic field intensity obtained by finite element method, which indicates that the present invention is applicable to the simulation of magnetic flux leakage.

Step S2: Simulation of magnetic flux leakage based on loop current on the condition of omitting the interacting forces between solenoids According to the theory of molecular current, assuming that the loop currents in the specimen are homogeneous, when the specimen is placed in the excitation magnetic field which is uniform and has a same direction with the positive direction of the x-axis.

Figure 2:
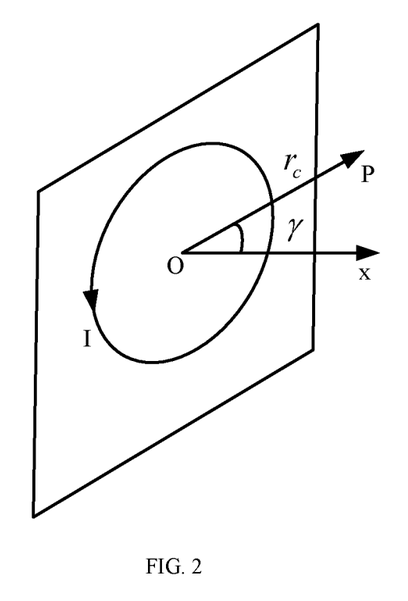
FIG. 2 is a diagram of the coordinate system of a loop current.

Step S2.1: Calculation of the magnetic field distribution of a semi-infinite solenoid In one embodiment, as shown in FIG. 2, obtaining a magnetic flux density $\vec{B}_{cp}$ generated by a loop current at a point P, where the point P is in the half-space that the magnetic moment of the loop current points to, and the magnetic flux density $\vec{B}_{cp}$ is:

$$\vec{B}_{cp} = -\frac{\mu_0 I}{4\pi} \nabla \Omega \qquad (2)$$

where $\Omega = (S \cos \gamma)/r_c^2$ is the solid angle from the point P to the loop current, S is the area encircled by the loop current, $r_c$ is the distance from the center of the loop current to the point P, $\gamma$ is the angle between the axis of the loop current and the line connecting the point P and the center of the loop current, and I is the value of the loop current, $\mu_0$ is the permeability of vacuum, $\pi$ is Pi.

In the contrary half-space, comparing to equation (1), there is a minus sign in the magnetic flux density generated by a loop current at a point P.

Figure 3:
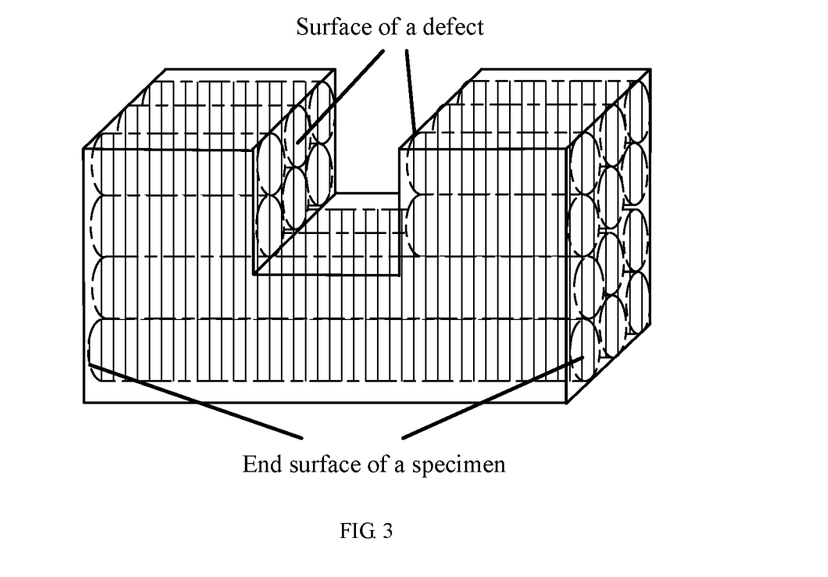
FIG. 3 is a diagram of the distribution of the solenoids in a defective specimen.

Assuming that a series of the loop currents are densely arranged along the direction of magnetization in the specimen forming a solenoid, thus a series of the solenoids are densely arranged in the specimen. In one embodiment, as shown in FIG. 3, when no defect exists on the specimen, there is no magnetic flux leakage, when there is a defect on the specimen, the solenoids part at the surface of the defect, and that results in the leakage of magnetic field lines into the air. Thus, the interior of the specimen is regarded as a black-box, the internal information does not influence the leakage generated by the surface of the defect, and the specimen just provides an access for leakage along the direction of loop current's magnetic moment, the leakage field is connected with the specimen by the surface of the defect. To introduce the impact of internal loop current in the specimen, a semi-infinite solenoid is used as the source of the leakage field. From the point of geometry, the solenoid could also be regarded as an element at the surface of the defect. It is assumed that the value of the loop current at the surface of the defect equals to the value of the corresponding semi-infinite solenoid which the loop current belongs to.

Figure 4:
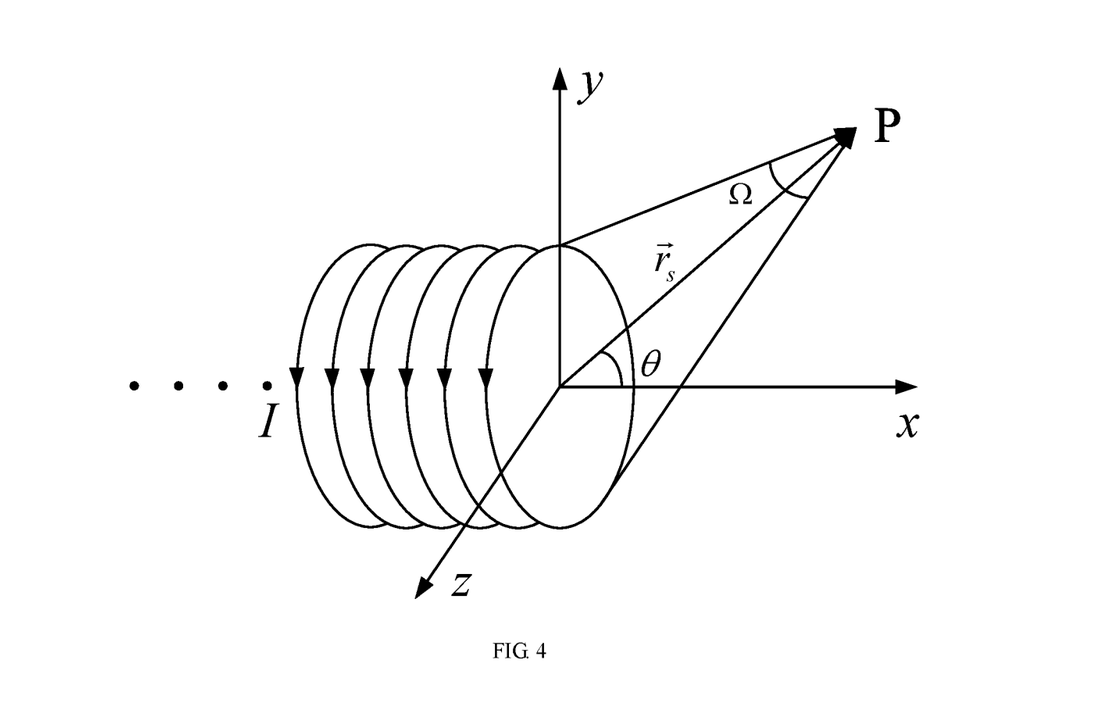
FIG. 4 is a diagram of the coordinate system of a semi-infinite solenoid.

In one embodiment, as shown in FIG. 4, there is a semi-infinite solenoid which axis is located in the negative half part of the x-axis, the positive direction of the x-axis is the direction of magnetic moment of the loop current, the center of its end surface is located at the origin of the coordinate, the distance from a field point P to the origin of the coordinate is r. The coordinate of the field point P is set as $(x^*, y^*, z^*)$, a element $dx_0^*$ at the place of $x_0^*$ is taken for integral, its coordinate is $(x_0^*, 0, 0)$. The linear density of the loop currents arranged in the semi-infinite solenoid is n, and the value of the loop current is I. The current related to $dx_0^*$ is $dI = n I dx_0^*$ According to equation (1), do integral on $x_0^*$ from minus infinity to 0, and substitute $r = \sqrt{(x^* x_0^*)^2 + y^{*2} + z^{*2}}$ to equation (1) to obtain a magnetic flux density $\vec{B}_{sp}$ generated by a semi-infinite solenoid in the air domain:

$$\vec{B}_{sp} = \frac{\mu_0 n P_m}{4\pi} \frac{\vec{r}_s}{r_s^3} \qquad (3)$$

where n is the linear density of the loop currents arranged in the semi-infinite solenoid, $\vec{P}_m$ is the magnetic moment of the loop currents arranged in the semi-infinite solenoid, the modulus of magnetic moment $\vec{P}_m$ is $P_m$, $P_m = SI$, and the relation between the direction of the magnetic moment $\vec{P}_m$ and the screw direction of the loop currents comply with the right hand screw rule, $\vec{r}_s$ is a vector from the end point of the semi-infinite solenoid to field point, and $r_s$ is the modulus of $r_s$.

Figure 5A:
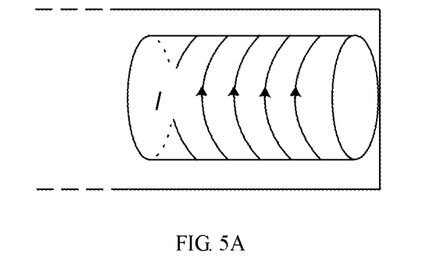
FIG. 5A is a diagram of a perpendicular relation between a solenoid and a surface.
Figure 5B:
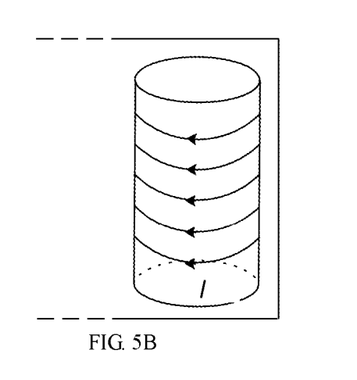
FIG. 5B is a diagram of a parallel relation between a solenoid and a surface.

The loop currents are located at every interface between magnetic media and air, so there are two extremely cases: the axial direction of the semi-infinite solenoid is perpendicular to the interface or parallel to the interface as shown in FIG. 5. In case as shown in FIG. 5A, the axial direction of solenoid is perpendicular to the interface, the magnetic flux completely leaks; It is likely that the solenoid is directly placed in air, and its impact on leakage field is the same as the magnetic field generated by it in vacuum. In another case as shown in FIG. 5B, when the axial direction of the semi-infinite solenoid and the interface are parallel, the magnetic flux completely does not leak, and the contribution of semi-infinite solenoid to magnetic field distribution is zero.

Therefore, a solenoid with any angle to the interface can be decomposed to the normal and tangential direction of the interface. the component of the magnetic moment $\vec{P}_m$ in the direction of the normal vector $\vec{m}$ of the surface of the defect is taken as an effective component $\vec{P}_{me}$, i.e. $P_{me} = \vec{P}_m \cdot \vec{m}$, where $\vec{m}$ points to air domain. $\theta$ is the angle between $\vec{P}_m$ and $\vec{m}$, when $\theta < 90°$, $\vec{P}_{me}$ is positive and the direction of the loop current is clockwise, which corresponds to positive magnetic charge; when $\theta > 90°$, $\vec{P}_{me}$ is negative and the direction of the loop current is anticlockwise, which corresponds to negative magnetic charge. This conclusion is agreed with the above result that the direction of loop current corresponds to the sign of magnetic charge. Thus, a magnetic flux density $\vec{P}_{ls}$ generated by an area on the surface of the defect or other interface where a loop current is located:

$$\vec{B}_{ls} = \frac{\mu_0 n P_{me}}{4\pi} \frac{\vec{r}_s}{r_s^3} \qquad (4)$$

According to the relation of magnetic flux density and magnetic field intensity in vacuum, i.e. $\vec{B}_{ls} = \mu_0 \vec{H}_{ls}$, obtaining a magnetic field intensity $\vec{H}_{ls}$ generated by an area on the surface of the defect where a loop current is located:

$$\vec{H}_{ls} = \frac{n P_{me}}{4\pi} \frac{\vec{r}_s}{r_s^3} \qquad (5)$$

Applying the calculation of equation (5) to other surfaces of the specimen, thus, obtaining the magnetic field distribution of semi-infinite solenoids.

Step S2.2: Simulation of magnetic flux leakage on the condition of introducing JA hysteresis model and omitting the interacting forces between solenoids;

First, establishing the relation between magnetic field intensity $H_{ex}$ and magnetization $M_d$ at the surface of a defect under quasi-static excitation.

Among the quasi-static models, it is needed to introduce magnetization model to describe the magnetization and magnetic field intensity at the surface of a defect. For nonlinear magnetization, there are many models including Jiles-Atherton model, Preisach model, StonerWolhfarth model, Globus model, their theoretical hypothesis, performance and applicability are different. considered that the specimen detected is ferromagnetic material, to get the hysteresis loop rapidly, the JA hysteresis model is chosen in present invention.

In present invention, a JA hysteresis model is used to establish the relation between magnetic field intensity and magnetization at the surface of a defect under quasi-static excitation:

$$\frac{dM_d}{dH_{ex}} = \frac{1}{1+c} \frac{1}{\frac{k\delta}{\mu_0} - \alpha(M_{an} - M_d)} (M_{an} - M_d) + \frac{c}{1+c} \frac{dM_{an}}{dH_{ex}} \quad (6)$$

$$\frac{dM_{an}}{dH_{ex}} = \frac{M_s}{a} \left( \frac{-1}{\sinh^2\left(\frac{H_{ex} + \alpha M_d}{a}\right)} + \frac{a^2}{(H_{ex} + \alpha M_d)^2} \right) \quad (7)$$

where c, k, α, a, $M_s$ are the parameters determined by the material property of the specimen; g is magnetization direction factor. When $dH_s/dt>0$, θ is 1, otherwise is −1; d is differential symbol. $\vec{M}_d = \Sigma \vec{P}_m/\Delta V$, where $\Delta V$ is the unit volume, $M_d$ is the modulus of $\vec{M}_d$. $M_{an}$ is non-hysteresis magnetization under ideal condition.

It is assumed that the direction of excitation magnetic field is constant. substituting the intensity value $H_{ex}$ of the excitation magnetic field into a JA hysteresis model, and the magnetization value $M_d$ at the surface of the defect is obtained.

As the direction of $\vec{H}_{ex}$ is the same as that of $\vec{M}_d$, $\vec{M}_d$ can be determined. For $\vec{M}_d = \Sigma \vec{P}_m/\Delta V$, according to the definition of $P_{me}$, then the effective component of magnetization can be calculated by $M_{de} = \vec{M}_d \cdot \vec{m}$, where $\vec{m}$ is the normal vector $\vec{m}$ of the surface of the defect.

According to Equation (5), the magnetic field density $\vec{H}_{ld}$ at point A in the magnetic flux leakage field generated by a element ds at the surface of the defect is:

$$\vec{H}_{ld} = \frac{M_{de}}{4\pi} \frac{\vec{r}_l}{r_l^3} ds \quad (6)$$

where $\vec{r}_l$ is the vector from ds to point A, and $r_l$ is the modulus of $\vec{r}_l$.

Thus, a contribution of a element on the surface of a defect to magnetic flux leakage is obtained. Meanwhile, taking the end surface of the specimen as a surface of the defect and applying the equation (6) to the end surface of the specimen, the a contribution of a element on the end surface of the specimen to magnetic flux leakage is obtained. Then integrating along the surface of the defect and the end surface of the specimen, and the distribution of quasi-static magnetic flux leakage field is obtained, i.e. simulation of magnetic flux leakage is finished on the condition of omitting the interacting forces between solenoids.

Step S3: Simulation of magnetic flux leakage on the condition of introducing interacting forces between solenoids at the surface of the specimen.

For the JA hysteresis model have introduced the influence of magnetization from magnetization process of ferromagnetic material, it is assumed that the interacting forces between solenoids would just change the direction of magnetization of the solenoids, but not their amplitudes. Then the effective component of magnetic moment would be changed.

Figure 6:
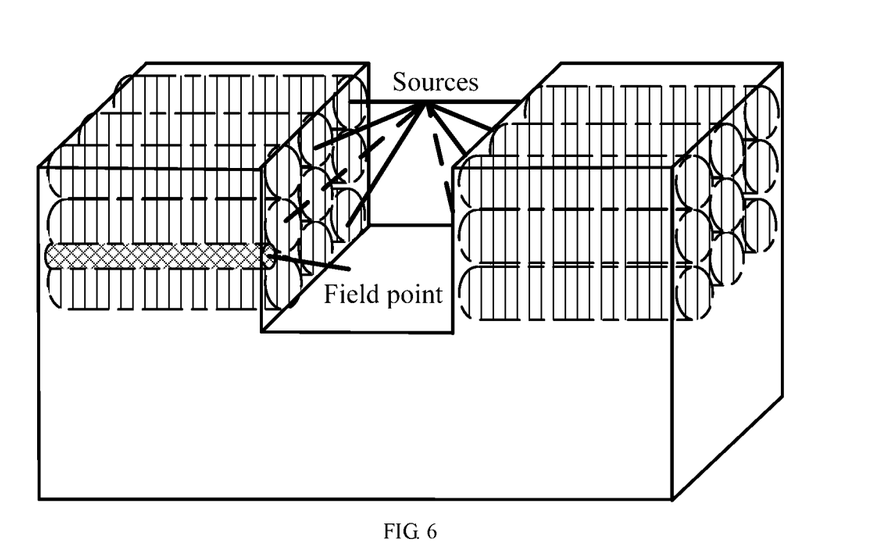
FIG. 6 is a diagram of a field point and the sources of interacting forces at the surface of a defect.

It is assumed that the force to a solenoid is proportional to the magnetic field intensity at its location generated by other solenoids and excitation magnetic field. When the effective component of magnetic moment is positive, the direction of action force is the same as magnetic field intensity, otherwise they are opposite. To simplify the computation and omit the influence of the edge of the surface of the defect, the continuous distribution of the solenoids at the surface of a defect should be discrete. As shown in FIG. 6, the surface of the defect is separated into two parts based on positive and negative effective component of the magnetization, and 3×3 solenoids are equally arranged at the two parts to simulating the sources of interacting forces, where the value of the effective component of the magnetization is the magnetization value $M_{s\_sp}$ of the saturation area of the specimen.

calculating the effective component of the magnetization of each solenoid at the surface of the defect under the action of the excitation magnetic field based on JA hysteresis model, and taking the sign of the effective component of the magnetization of each solenoid, a new effective magnetization of each solenoid is obtained by combing the sign with the magnetization value $M_{s\_sp}$. then calculating the magnetic field density $\vec{H}_{ld}$ under the action of the excitation magnetic field and the 3×3 sources of interacting forces according to equation (6), taking the direction of the magnetic field density $\vec{H}_{ld}$ as the direction of magnetization $\vec{M}_d$, a corrected effective component $M_{de}$ of magnetization $\vec{M}_d$ is obtained, i.e. $M_{de} = \vec{M}_d \cdot \vec{m}$, where $\vec{m}$ is the normal vector $\vec{m}$ of the surface of the defect.

the solenoid model is derived in the condition that field point is far from the solenoid, the calculation of magnetic field density around sources of interacting force has a certain error. So in present invention, a rectangle is created for each source, where the rectangle is adjacent to the outline of source, the corrected effective component of magnetization in a rectangle is set to the mean value of those of its four sides, thus, a final corrected effective component $M_{de}$ of magnetization is obtained.

Applying equation (6) to the surface of the defect and the end surface of the specimen with the final corrected effective component $M_{de}$ of magnetization, and integrating along the surface of the defect and the end surface of the specimen, thus the distribution of quasi-static magnetic flux leakage field is obtained on the condition of introducing the interacting forces between solenoids, i.e. simulation of magnetic flux leakage.

Figure 7:
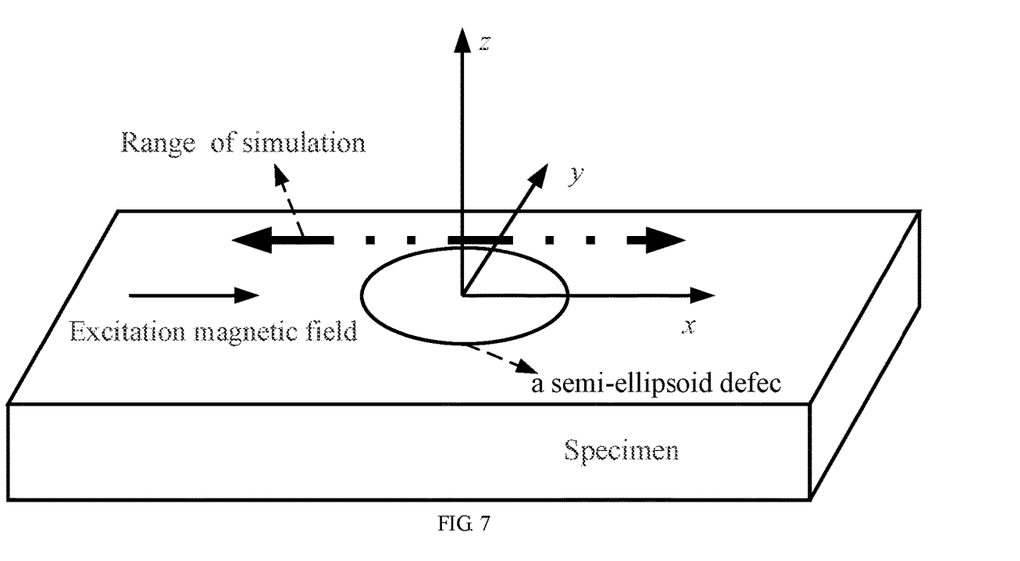
FIG. 7 is a diagram of simulating magnetic flux leakage according to one embodiment of the present invention.
Figure 8:
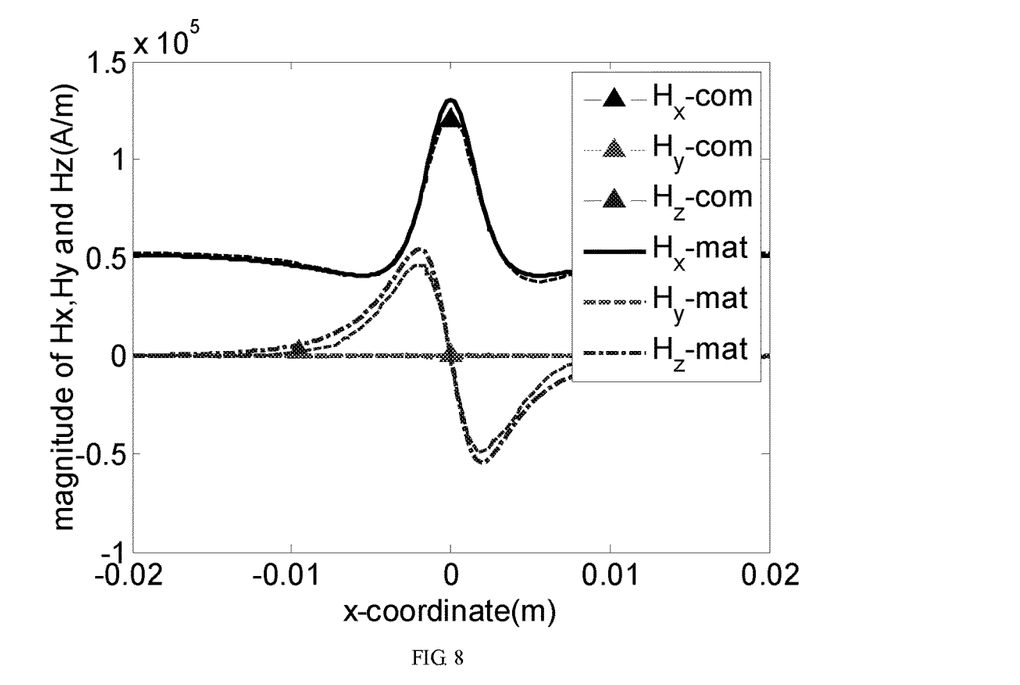
FIG. 8 is a diagram of a comparison between a conventional method and the present invention.

In one embodiment, a rectangular specimen which sizes along x-axis, y-axis and z-axis are 0.15 m, 0.1 m and 0.006 m respectively is placed at the excitation magnetic field, the magnetic field intensity of the excitation magnetic field is $7.2 \times 10^4$ A/m, and the direction of the excitation magnetic field is the positive direction of an x-axis. The center of the specimen's top surface is located at the originate of the coordinate where there is a semi-ellipsoid defect with lengths 1 mm, 8 mm and 6 mm along x-axis, y-axis and z-axis respectively, as shown in FIG. 7. In the plane of yoz, where z=0.002 m, x=−0.02~0.02 m, the magnetic field intensity is calculated by the present invention, and the result is shown in FIG. 8. The line marked with triangle is the result from FEM, the other line without mark is the that from the present invention, and the maximum relative error of the component along x-axis of magnetic field intensity is 4.65%, and along z-axis it is 18.26%.

While illustrative embodiments of the invention have been described above, it is, of course, understand that various modifications will be apparent to those of ordinary skill in the art. Such modifications are within the spirit and scope of the invention, which is limited and defined only by the appended claims.

What is claimed is:

1. A method for simulating magnetic flux leakage based on loop current, comprising the following steps:
   (1) establishing homogeneous magnetization of a specimen, the specimen being a flat ferromagnetic specimen, by:
      placing the specimen in an excitation magnetic field, where the excitation magnetic field is uniform, a direction of the excitation magnetic field is a positive direction of an x-axis, an intensity value of the excitation magnetic field is $H_{ex}$, and when a magnetization value of a saturation area of the specimen is $M_{s\_sp}$ and a proportion of the saturation area of the specimen is $k_s$, the specimen is regarded as a homogeneous magnetized body;
      applying a solenoid model to end faces of the specimen, and under an interaction between the excitation magnetic field and the end faces of the specimen, a magnetic field intensity $\vec{H}_{air}$ at a borderline between the saturation area and an insaturation area of the specimen in the air is:

$$\vec{H}_{air} = \vec{H}_{ex} + (M_{s\_sp} \vec{r}_{air} ds)/(4\pi r_{air}^3) \quad (1)$$

where $\vec{H}_{ex}$ is the intensity of the excitation magnetic field, $\vec{r}_{air}$ is a vector from an end face element ds to a point in air domain;
   substituting an x-axis component $\vec{H}_{x\_sp}$ of the magnetic field intensity in the specimen into a Jiles Atherton (JA) hysteresis model, and obtaining the magnetization $\vec{M}_{x\_sp}$ in the specimen, where the x-axis component $\vec{H}_{x\_sp}$ is equal to the x-axis component $\vec{H}_{x\_air}$ of magnetic field intensity $\vec{H}_{air}$; and
   taking the specimen as a homogeneous magnetized body which is already saturated, when $M_{x\_sp} > k_M * M_{s\_sp}$, where $k_M$ is a proportionality constant which is smaller than 1, and the proportionality constant $k_s$ and $k_M$ are determined by the precision of magnetic flux leakage simulation, and the larger the proportionality constant $k_s$ and $k_M$ are, the more precise the simulation is;

(2) simulating magnetic flux leakage based on loop current on the condition of omitting the interacting forces between solenoids,
according to a theory of molecular current, taking the loop currents in the specimen as homogeneous, when the specimen is placed in the excitation magnetic field which is uniform and has a same direction with the positive direction of the x-axis, by:
2.1) calculating a magnetic field distribution of a semi-infinite solenoid by:
   obtaining a magnetic flux density $\vec{B}_{cp}$ generated by a loop current at a point P, where the point P is in the half-space that a magnetic moment of the loop current points to, and the magnetic flux density $\vec{B}_{cp}$, is:

$$\vec{B}_{cp} = -\frac{\mu_0 I}{4\pi} \nabla \Omega \quad (2)$$

where $\Omega = (S \cos \gamma)/r_c^2$ is a solid angle from the point P to the loop current, S is the area encircled by the loop current, $r_c$ is the distance from the center of the loop current to the point P, $\gamma$ is an angle between the axis of the loop current and the line connecting the point P and the center of the loop current, and I is a value of the loop current, $\mu_0$ is a permeability of vacuum, $\pi$ is Pi;
   taking a series of the loop currents as densely arranged along a direction of magnetization in the specimen forming a solenoid, thus a series of the solenoids are densely arranged in the specimen, and when no defect exists on the specimen, there is no magnetic flux leakage, when there is a defect on the specimen, the value of the loop current at a surface of the defect equals to the value of the corresponding solenoid which the loop current belongs to, and the length of the corresponding solenoid is semi-infinite;
   integrating the equation (2), and obtaining a magnetic flux density $\vec{B}_{sp}$ generated by a semi-infinite solenoid in the air domain:

$$\vec{B}_{sp} = \frac{\mu_0 n P_m}{4\pi} \frac{\vec{r}_s}{r_s^3} \quad (3)$$

where n is a linear density of the loop currents arranged in the semi-infinite solenoid, $\vec{P}_m$ is the magnetic moment of the loop currents arranged in the semi-infinite solenoid, a modulus of the magnetic moment $\vec{P}_m$ is $P_m$, $P_m = SI$, and a relation between a direction of the magnetic moment $\vec{P}_m$ and a screw direction of the loop currents comply with the right hand screw rule, $\vec{r}_s$ is a vector from the end point of the semi-infinite solenoid to a field point, and $r_s$ is a modulus of $\vec{r}_s$;
   where if the axial direction of the semi-infinite solenoid is perpendicular to the surface of the defect, the magnetic flux completely leaks, and if the axial direction of the semi-infinite solenoid and the surface of the defect are parallel to each other, the magnetic flux completely does not leak;

taking the component of the magnetic moment i in the direction of a normal vector $\vec{m}$ of the surface of the defect as an effective component $\vec{P}_{me}$, wherein $P_{me} = \vec{P}_m \cdot \vec{m}$, where $\vec{m}$ points to air domain, thus, obtaining a magnetic flux density $\vec{B}_{ls}$ generated by an area on the surface of the defect where a loop current is located:

$$\vec{B}_{ls} = \frac{\mu_0 n P_{me}}{4\pi} \frac{\vec{r}_s}{r_s^3} \qquad (4)$$

according to a relation of magnetic flux density and magnetic field intensity in vacuum, where $\vec{B}_{ls} = \mu_0 \vec{H}_{ls}$, obtaining a magnetic field intensity $\vec{H}_{ls}$ generated by an area on the surface of the defect where a loop current is located:

$$\vec{H}_{ls} = \frac{n P_{me}}{4\pi} \frac{\vec{r}_s}{r_s^3} \qquad (5)$$

applying the calculation of equation (5) to other surfaces of the specimen, thereby obtaining the magnetic field distribution of semi-infinite solenoids, 2.2) simulating magnetic flux leakage on the condition of introducing the JA hysteresis model and omitting the interacting forces between solenoids, by:

substituting the intensity value H of the excitation magnetic field into the JA hysteresis model, and calculating a magnetization value $M_d$ at the surface of the defect, thus obtaining a magnetization $\vec{M}_d$ at the surface of the defect, for the direction of the intensity $\vec{H}_{ex}$ of the excitation magnetic field is the same as that of the magnetization $\vec{M}_d$, then obtaining an effective component $M_{dc}$ of magnetization $\vec{M}_d$, wherein $M_{de} = \vec{M}_d \cdot \vec{m}$, where $\vec{m}$ is the normal vector m of the surface of the defect;

obtaining a magnetic field density $\vec{H}_{ld}$ at point A in the magnetic flux leakage field generated by an element ds at the surface of the defect according to equation (5):

$$\vec{H}_{ld} = \frac{M_{de}}{4\pi} \frac{\vec{r}_l}{r_l^3} ds \qquad (6)$$

where $\vec{r}$ is a vector from ds to point A, and $r_l$ is a modulus of $\vec{r}_l$; and thus obtaining a contribution of an element on the surface of a defect to magnetic flux leakage, meanwhile, taking an end surface of the specimen as a surface of a defect and applying equation (6) to the end surface of the specimen, obtaining a contribution of an element on the end surface of the specimen to magnetic flux leakage, then integrating along the surface of the defect and the end surface of the specimen, and obtaining a distribution of quasi-static magnetic flux leakage field on the condition of omitting the interacting forces between solenoids, thereby simulating magnetic flux leakage;

(3) simulating magnetic flux leakage on a condition of introducing interacting forces between solenoids at the end surface of the specimen by:

separating the surface of the defect into two parts based on positive and negative effective component of the magnetization, and equally arranging 3×3 solenoids at the two parts to simulating the sources of interacting forces, where the value of an effective component of the magnetization is the magnetization value $M_{s\_sp}$ of the saturation area of the specimen;

calculating the effective component of the magnetization of each solenoid at the surface of the defect under the action of the excitation magnetic field based on JA hysteresis model, taking a sign of the effective component of the magnetization of each solenoid, and obtaining a new effective magnetization of each solenoid by combing the sign with the magnetization value $M_{s\_sp}$, then calculating the magnetic field density $\vec{H}_M$ under the action of the excitation magnetic field and the 3×3 sources of interacting forces according to equation (6), taking the direction of the magnetic field density $\vec{H}_M$ as the direction of magnetization $\vec{M}_d$ and obtaining a corrected effective component $M_{dc}$ of magnetization $\vec{H}_d$, wherein $M_{de} = \vec{M}_d \cdot \vec{m}$, where $\vec{m}$ is the normal vector $\vec{m}$ of the surface of the defect;

creating a rectangle for each source, where the rectangle is adjacent to the outline of source, setting a corrected effective component of magnetization in a rectangle to a mean value of four sides of the rectangle, thus, obtaining a final corrected effective component $M_{dc}$ of magnetization; and applying equation (6) to the surface of the defect and the end surface of the specimen with the final corrected effective component $M_{dc}$ of magnetization, and integrating along the surface of the defect and the end surface of the specimen, thus obtaining the distribution of quasi-static magnetic flux leakage field on the condition of introducing the interacting forces between solenoids, thereby simulating magnetic flux leakage.

2. The method for simulating magnetic flux leakage based on loop current according to claim 1, wherein the proportion of the saturation area of the specimen $k_s$ equals to ¾, and the proportionality constant $K_M$ equals to 0.95.

* * * * *